(12) United States Patent
Kuzma

(10) Patent No.: US 7,445,528 B1
(45) Date of Patent: Nov. 4, 2008

(54) CONNECTOR ASSEMBLIES

(75) Inventor: Janusz Kuzma, Bayview (AU)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 11/541,117

(22) Filed: Sep. 29, 2006

(51) Int. Cl.
*H01R 13/05* (2006.01)

(52) U.S. Cl. .................. 439/825; 439/930; 439/369

(58) Field of Classification Search .......... 439/825, 439/827, 930, 369
See application file for complete search history.

(56) References Cited

U.S. PATENT DOCUMENTS

| | | | |
|---|---|---|---|
| 2,036,759 A * | 4/1936 | Kleinmann | 439/825 |
| 2,780,792 A * | 2/1957 | Earl | 439/750 |
| 3,107,966 A | 10/1963 | Bonhomme | |
| 3,581,272 A * | 5/1971 | Yopp et al. | 439/825 |
| 3,760,984 A | 9/1973 | Theeuwes | |
| 3,845,770 A | 11/1974 | Theeuwes et al. | |
| 3,916,899 A | 11/1975 | Theeuwes et al. | |
| 3,923,426 A | 12/1975 | Theeuwes | |
| 3,987,790 A | 10/1976 | Eckenhoff et al. | |
| 3,995,631 A | 12/1976 | Higuchi et al. | |
| 4,016,880 A | 4/1977 | Theeuwes et al. | |
| 4,036,228 A | 7/1977 | Theeuwes | |
| 4,111,202 A | 9/1978 | Theeuwes | |
| 4,111,203 A | 9/1978 | Theeuwes | |
| 4,203,440 A | 5/1980 | Theeuwes | |
| 4,203,442 A | 5/1980 | Michaels | |
| 4,210,139 A | 7/1980 | Higuchi | |
| 4,327,725 A | 5/1982 | Cortese et al. | |
| 4,360,019 A | 11/1982 | Portner et al. | |
| 4,459,989 A | 7/1984 | Borkan | |
| 4,487,603 A | 12/1984 | Harris | |
| 4,562,751 A | 1/1986 | Nason et al. | |
| 4,627,850 A | 12/1986 | Deters et al. | |
| 4,678,408 A | 7/1987 | Nason et al. | |
| 4,685,903 A | 8/1987 | Cable et al. | |
| 4,692,147 A | 9/1987 | Duggan | |
| 4,725,852 A | 2/1988 | Gamblin et al. | |
| 4,865,845 A | 9/1989 | Eckenhoff et al. | |

(Continued)

FOREIGN PATENT DOCUMENTS

WO    WO 01/82398 A1    1/2001
WO    WO 03/005465 A1   1/2003

OTHER PUBLICATIONS

Wikipedia entry entitled "Banana connector." Printed Nov. 1, 2007. Available at http://en.wikipedia.org/wiki/Banana_connector.

(Continued)

*Primary Examiner*—Javaid Nasri
(74) *Attorney, Agent, or Firm*—Fish & Richardson P.C.

(57) ABSTRACT

Systems for electrically coupling two or more devices include a receptacle connector assembly and a male connector assembly. The receptacle connector assembly includes one or more socket assemblies each having a socket with an at least partially conductive inner surface. The male connector assembly includes one or more plug contacts configured to mate with the sockets. Each of the plug contacts includes a multiplicity of compressible wires joined together at a distal tip such that when the plug contacts are inserted within the sockets, the compressible wires make electrical contact with the at least partially conductive inner surfaces of the sockets.

26 Claims, 10 Drawing Sheets

U.S. PATENT DOCUMENTS

| | | | |
|---|---|---|---|
| 4,886,471 A | 12/1989 | Fleshman Jr. | |
| 4,941,472 A | 7/1990 | Moden et al. | |
| 4,959,022 A * | 9/1990 | Neuroth | 439/589 |
| 5,057,318 A | 10/1991 | Magruder et al. | |
| 5,059,423 A | 10/1991 | Magruder et al. | |
| 5,080,653 A | 1/1992 | Voss et al. | |
| 5,097,122 A | 3/1992 | Colman et al. | |
| 5,112,614 A | 5/1992 | Magruder et al. | |
| 5,137,727 A | 8/1992 | Eckenhoff | |
| 5,193,539 A | 3/1993 | Schulman et al. | |
| 5,193,540 A | 3/1993 | Schulman et al. | |
| 5,203,813 A | 4/1993 | Fitzsimmons et al. | |
| 5,234,692 A | 8/1993 | Magruder et al. | |
| 5,234,693 A | 8/1993 | Magruder et al. | |
| 5,273,443 A | 12/1993 | Frantz et al. | |
| 5,312,439 A | 5/1994 | Loeb | |
| 5,427,541 A | 6/1995 | Calio | |
| 5,501,703 A | 3/1996 | Holsheimer | |
| 5,728,396 A | 3/1998 | Peery et al. | |
| 5,938,688 A | 8/1999 | Schiff | |
| 5,951,595 A | 9/1999 | Moberg et al. | |
| 6,016,449 A | 1/2000 | Fischell et al. | |
| 6,051,017 A | 4/2000 | Loeb et al. | |
| 6,052,624 A | 4/2000 | Mann | |
| 6,070,103 A | 5/2000 | Ogden | |
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,219,580 B1 | 4/2001 | Faltys et al. | |
| 6,272,382 B1 | 8/2001 | Faltys et al. | |
| 6,280,873 B1 | 8/2001 | Tsukamoto | |
| 6,308,101 B1 | 10/2001 | Faltys et al. | |
| 6,368,315 B1 | 4/2002 | Gillis et al. | |
| 6,381,496 B1 | 4/2002 | Meadows et al. | |
| 6,428,368 B1 | 8/2002 | Hawkins et al. | |
| 6,458,171 B1 | 10/2002 | Tsukamoto | |
| 6,487,446 B1 | 11/2002 | Hill et al. | |
| 6,516,227 B1 | 2/2003 | Meadows et al. | |
| 6,539,263 B1 | 3/2003 | Schiff et al. | |
| 6,553,263 B1 | 4/2003 | Meadows et al. | |
| 6,620,151 B2 | 9/2003 | Blischak et al. | |
| 6,666,845 B2 | 12/2003 | Hooper et al. | |
| 6,740,072 B2 | 5/2004 | Starkweather et al. | |
| 6,760,626 B1 | 7/2004 | Boveja | |
| 6,770,067 B2 | 8/2004 | Lorenzen et al. | |
| 6,796,803 B2 | 9/2004 | Abe | |
| 7,347,746 B1 | 3/2005 | He | |
| 2001/0046625 A1 | 11/2001 | Ruth, II et al. | |
| 2001/0053476 A1 | 12/2001 | Ruth et al. | |

OTHER PUBLICATIONS

The Tech-faq.com document entitled "What are Banana Plugs?" Printed Nov. 1, 2007. Available at http://www.tech-faq.com/banana-plugs.shtml.

Mueller Electric Co. document entitled "Banana Plugs." Copyright 2005. Printed Nov. 1, 2007. Available at http://www.muellerelectric.com/banana_plugs.html.

Abbatron document entitled "Insulated Banana Plugs, Miscellaneous." Copyright 2006. Printed Nov. 1, 2007, Available at http://www.abbatron.com/products/?dir=/part/get/ppj_ubp_thrd.

Abbatron document entitled "Insulated Banana Plugs." Copyright 2006. Printed Nov. 1, 2007. Available at http://www.abbatron.com/products/?dir=/part/get/ppj_ibp_stnd.

Abbatron document entitled "Standard Insulated Banana Plugs, Solderless." Copyright 2006. Printed Nov. 1, 2007. Available at http://www.abbatron.com/products/?dir=/part/get/ppj_ibp_sles.

Abbatron document entitled "Giant Uninsulated Banana Plug." Copyright 2006. Printed Nov. 1, 2007. Available at http://www.abbatron.com/products/?dir=/part/get/ppj_ubp_gian.

Abbatron document entitled "Rivet Stud Uninsulated Banana Plug." Copyright 2006. Printed Nov. 1, 2007. Available at http://www.abbatron.com/products/?dir=/part/get/ppj_ubp_rivt.

Abbatron document entitled "Threaded Uninsulated Banana Plugs." Copyright 2006. Printed Nov. 1, 2007, Available at http://www.abbatron.com/products/?dir=/part/get/ppj_ubp_thrd.

* cited by examiner

CONNECTOR ASSEMBLIES

BACKGROUND

A wide variety of medical conditions and disorders have been successfully treated using implantable medical devices. Such implantable devices include, but are not limited to, stimulators, pacemakers, and defibrillators.

It is often desirable to electrically couple an implantable medical device to another device. For example, an implantable device may be coupled to a lead having a number of electrodes disposed thereon so that the device may deliver electrical stimulation to a site within the body. Additionally or alternatively, an implantable device may be electrically coupled to an external device configured to communicate with and support the implantable device.

To facilitate electrical coupling to another device, many implantable devices include one or more connector assemblies. A common type of connector assembly includes an array of pins configured to detachably mate with a receptacle connector assembly having a corresponding pattern of female sockets or holes.

With advancements in technology, many implantable devices have become increasingly complex and smaller in size. Hence, the need for small, reliable pin array connectors and corresponding receptacle connectors has increased.

However, it is currently difficult and costly to manufacture small connectors for implantable medical devices because stringent dimensional and geometrical tolerance requirements must be met. Moreover, typical pin array connector assemblies have pins that are made out of rigid metal. This rigidity may result in undesirable stress when the pins and sockets are connected, and thereby cause device malfunction.

SUMMARY

Systems for electrically coupling two or more devices include a receptacle connector assembly and a male connector assembly. The receptacle connector assembly includes one or more socket assemblies each having a socket with an at least partially conductive inner surface. The male connector assembly includes one or more plug contacts configured to mate with the sockets. Each of the plug contacts includes a multiplicity of compressible wires joined together at a distal tip such that when the plug contacts are inserted within the sockets, the compressible wires make electrical contact with the at least partially conductive inner surfaces of the sockets.

Methods of electrically coupling two or more devices include providing a receptacle connector assembly and a male connector assembly. The receptacle connector assembly includes one or more socket assemblies each having a socket with an at least partially conductive inner surface. The male connector assembly includes one or more plug contacts each having a multiplicity of compressible wires joined to each other at a distal tip. The method further includes inserting the compressible wires of the plug contacts into the sockets such that the compressible wires make electrical contact with the at least partially conductive inner surfaces of the sockets.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Connector assemblies for electrically coupling two or more devices are described herein. A receptacle connector assembly includes one or more socket assemblies each having a socket with an at least partially conductive inner surface. A male connector assembly includes one or more plug contacts configured to mate with the sockets of the receptacle connector assembly. Each of the plug contacts includes a multiplicity (i.e., two or more) of compressible wires joined together at a distal tip such that when the plug contacts are inserted into the sockets, the compressible wires make electrical contact with the at least partially conductive inner surfaces of the sockets.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

As used herein and in the appended claims, the terms "implantable medical device," "implanted device" and variations thereof will be used broadly to refer to any type of device that is implanted within a patient to perform any function. For example, the implantable device may include, but is not limited to, a stimulator, pacemaker, sensor, or defibrillator.

It will be recognized that the connector assemblies described herein may be used with any device configured to be electrically coupled to another device and are not limited to use with implantable devices only. For example, the connector assemblies described herein may be used with computers, computer accessories, electro-mechanical devices, or any other device. However, for illustrative purposes only, implantable devices will be used in the examples described herein.

Figure 1:
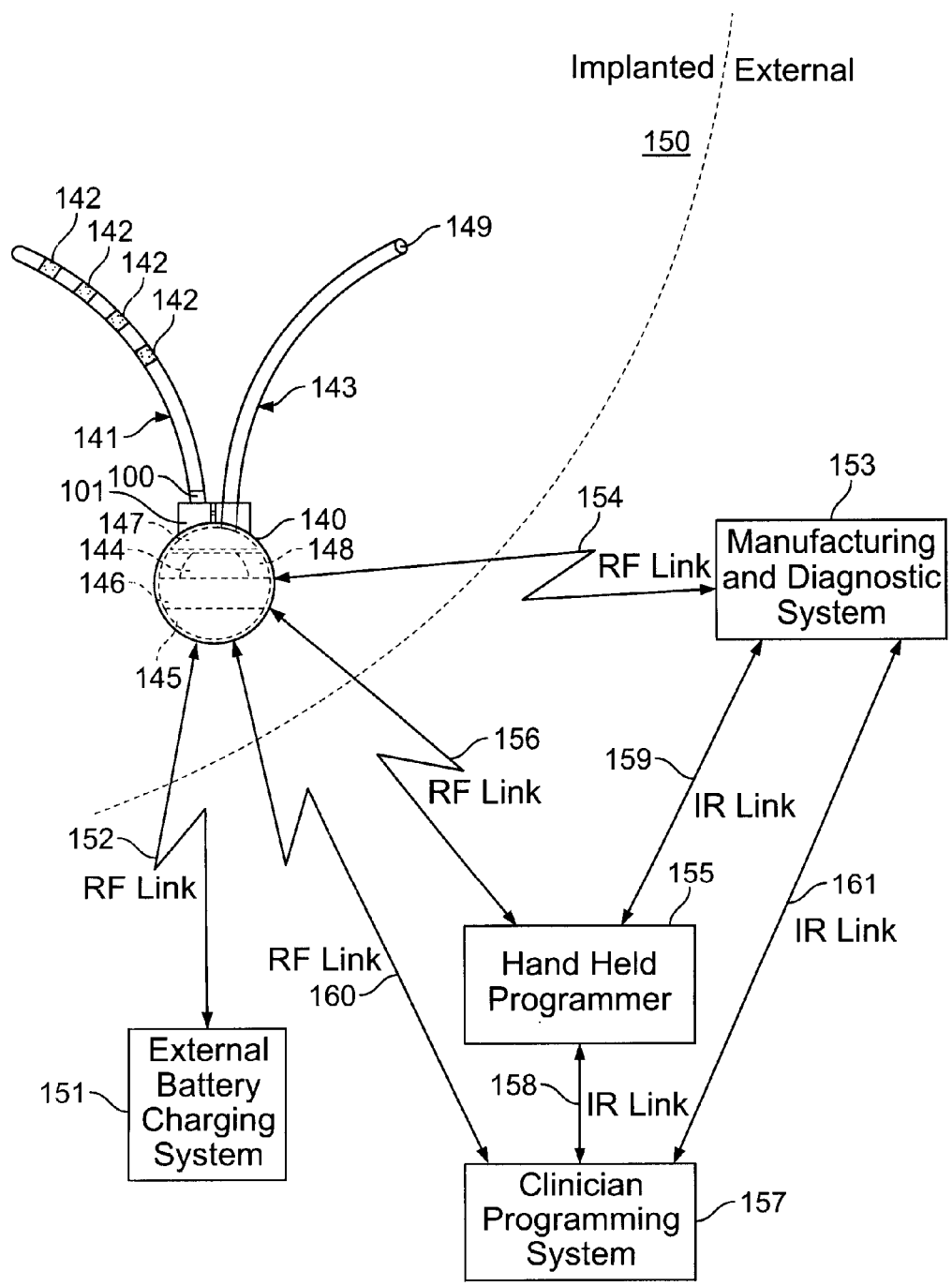
FIG. 1 illustrates an exemplary implantable device that may be used with one or more connector assemblies according to principles described herein.

To facilitate an understanding of an exemplary implantable medical device with which the connector assemblies described herein may be used, an exemplary implantable stimulator will now be described in connection with FIG. 1. FIG. 1 illustrates an implantable stimulator (140) that may be implanted within a patient (150) and used to apply a stimulus to a stimulation site, e.g., an electrical stimulation of the stimulation site, an infusion of one or more drugs at the stimulation site, or both. The electrical stimulation function of the stimulator (140) will be described first, followed by an explanation of the possible drug delivery function of the stimulator (140). It will be understood, however, that the stimulator (140) may be configured to provide only electrical stimulation, only a drug stimulation, both types of stimulation or any other type of stimulation as best suits a particular patient.

The exemplary stimulator (140) shown in FIG. 1 is configured to provide electrical stimulation to a stimulation site via a lead (141) having a number of electrodes (142) disposed thereon. The lead (141) may include any number of electrodes (142) as best serves a particular application. The electrodes (142) may be arranged as an array, for example, having at least two or at least four collinear electrodes. In some embodiments, the electrodes are alternatively inductively coupled to the stimulator (140). The lead (141) may be thin (e.g., less than 3 millimeters in diameter) such that the lead (141) may be positioned near a stimulation site. In some alternative examples, the stimulator (140) is leadless.

As shown in FIG. 1, the lead (141) may include at its proximal end a first connector assembly (100) configured to mate with a second connector assembly (101) that is a part of the stimulator (140). In this manner, the lead (141) may be electrically coupled to the stimulator (140). The stimulator (140) may include one or more additional or alternative connector assemblies configured to connect to one or more other devices. The connector assemblies (100, 101) will be described in more detail below.

As illustrated in FIG. 1, the stimulator (140) includes a number of components. It will be recognized that the stimulator (140) may include additional or alternative components as best serves a particular application. A power source (145) is configured to output voltage used to supply the various components within the stimulator (140) with power and/or to generate the power used for electrical stimulation. The power source (145) may be a primary battery, a rechargeable battery, super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like. Alternatively, the stimulator (140) may include one or more components configured to receive power from another medical device that is implanted within the patient.

When the power source (145) is a battery, it may be a lithium-ion battery or other suitable type of battery. When the power source (145) is a rechargeable battery, it may be recharged from an external system through a power link such as a radio frequency (RF) power link or a wire connection. One type of rechargeable battery that may be used is described in International Publication WO 01/82398 A1, published Nov. 1, 2001, and/or WO 03/005465 A1, published Jan. 16, 2003, both of which are incorporated herein by reference in their respective entireties. Other battery construction techniques that may be used to make a power source (145) include those shown, e.g., in U.S. Pat. Nos. 6,280,873; 6,458,171 and U.S. Publications 2001/0046625 A1 and 2001/0053476 A1, all of which are incorporated herein by reference in their respective entireties. Recharging can be performed using an external charger.

The stimulator (140) may also include a coil (148) configured to receive and/or emit a magnetic field (also referred to as a radio frequency (RF) field) that is used to communicate with, or receive power from, one or more external devices (151, 153, 155). Such communication and/or power transfer may include, but is not limited to, transcutaneously receiving data from the external device, transmitting data to the external device, and/or receiving power used to recharge the power source (145).

For example, an external battery charging system (EBCS) (151) may provide power used to recharge the power source (145) via an RF link (152). Additionally or alternatively, the EBCS (151) may provide power to the power source (145) via a direct wire link (not shown). External devices including, but not limited to, a hand held programmer (HHP) (155), clinician programming system (CPS) (157), and/or a manufacturing and diagnostic system (MDS)(153) may be configured to activate, deactivate, program, and test the stimulator (140) via one or more RF links (154, 156). It will be recognized that the links, which are RF links (152, 154, 156) in the illustrated example, may be any type of link used to transmit data or energy, such as an optical link, a thermal link, or any other energy-coupling link. One or more of these external devices (153, 155, 157) may also be used to control the infusion of one or more drugs into the stimulation site.

Additionally, if multiple external devices are used in the treatment of a patient, there may be some communication among those external devices, as well as with the implanted stimulator (140). Again, any type of link for transmitting data or energy may be used among the various devices illustrated. For example, the CPS (157) may communicate with the HHP (155) via an infrared (IR) link (158), with the MDS (153) via an IR link (161), and/or directly with the stimulator (140) via an RF link (160). As indicated, these communication links (158, 161, 160) are not necessarily limited to IR and RF links and may include any other type of communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the stimulator (140). Furthermore, it will be recognized that the functions performed by any two or more of the HHP (155), MDS (153), CPS (157), and EBCS (151) may be performed by a single external device. One or more of the external devices (153, 155, 157) may be embedded in a seat cushion, mattress cover, pillow, garment, belt, strap, pouch, or the like so as to be positioned near the implanted stimulator (140) when in use.

The stimulator (140) may also include electrical circuitry (144) configured to produce electrical stimulation pulses that are delivered to the stimulation site via the electrodes (142). In some embodiments, the stimulator (140) may be configured to produce monopolar stimulation. The stimulator (140)

may alternatively or additionally be configured to produce multipolar stimulation including, but not limited to, bipolar or tripolar stimulation.

The electrical circuitry (144) may include one or more processors configured to decode stimulation parameters and generate the stimulation pulses. In some embodiments, the stimulator (140) has at least four channels and drives up to sixteen electrodes or more. The electrical circuitry (144) may include additional circuitry such as capacitors, integrated circuits, resistors, coils, and the like configured to perform a variety of functions as best serves a particular application.

The stimulator (140) may also include a programmable memory unit (146) for storing one or more sets of data and/or stimulation parameters. The stimulation parameters may include, but are not limited to, electrical stimulation parameters, drug stimulation parameters, and other types of stimulation parameters. The programmable memory (146) allows a patient, clinician, or other user of the stimulator (140) to adjust the stimulation parameters such that the stimulation applied by the stimulator (140) is safe and efficacious for treatment of a particular patient. The different types of stimulation parameters (e.g., electrical stimulation parameters and drug stimulation parameters) may be controlled independently. However, in some instances, the different types of stimulation parameters are coupled. For example, electrical stimulation may be programmed to occur only during drug stimulation or vice versa. Alternatively, the different types of stimulation may be applied at different times or with only some overlap. The programmable memory (146) may be any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, waveform (e.g., square or sinusoidal), electrode configuration (i.e., anode-cathode assignment), burst pattern (e.g., burst on time and burst off time), duty cycle or burst repeat interval, ramp on time, and ramp off time of the stimulation current that is applied to the stimulation site. The drug stimulation parameters may control various parameters including, but not limited to, the amount of drugs infused at the stimulation site, the rate of drug infusion, and the frequency of drug infusion. For example, the drug stimulation parameters may cause the drug infusion rate to be intermittent, constant, or bolus. Other stimulation parameters that characterize other classes of stimuli are possible. For example, when tissue is stimulated using electromagnetic radiation, the stimulation parameters may characterize the intensity, wavelength, and timing of the electromagnetic radiation stimuli. When tissue is stimulated using mechanical stimuli, the stimulation parameters may characterize the pressure, displacement, frequency, and timing of the mechanical stimuli.

Specific stimulation parameters may have different effects on different stimulation sites and/or different patients. Thus, in some embodiments, the stimulation parameters may be adjusted by the patient, a clinician, or other user of the stimulator (140) as best serves the particular stimulation site or patient being treated. The stimulation parameters may also be automatically adjusted by the stimulator (140), as will be described below. For example, the stimulator (140) may increase excitement of a stimulation site, for example, by applying a stimulation current having a relatively low frequency (e.g., less than 100 Hz). The stimulator (140) may also decrease excitement of a stimulation site by applying a relatively high frequency (e.g., greater than 100 Hz). The stimulator (140) may also, or alternatively, be programmed to apply the stimulation current to a stimulation site intermittently or continuously.

Additionally, the exemplary stimulator (140) shown in FIG. 1 is configured to apply one or more drugs at a stimulation site within a patient. For this purpose, a pump (147) may also be included within the stimulator (140). The pump (147) is configured to store and dispense one or more drugs, for example, through a catheter (143). The catheter (143) is coupled at a proximal end to the stimulator (140) and may have an infusion outlet (149) for infusing dosages of the one or more drugs at the stimulation site. In some embodiments, the stimulator (140) may include multiple catheters (143) and/or pumps (147) for storing and infusing dosages of the one or more drugs at the stimulation site.

The pump (147) or controlled drug release device described herein may include any of a variety of different drug delivery systems. Controlled drug release devices based upon a mechanical or electromechanical infusion pump may be used. In other examples, the controlled drug release device can include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps. Another example is a micro-drug pump.

Exemplary pumps (147) or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. Additional exemplary drug pumps suitable for use as described herein include, but are not necessarily limited to, those disclosed in U.S. Pat. Nos. 4,562,751; 4,678,408; 4,685,903; 5,080,653; 5,097,122; 6,740,072; and 6,770,067. Exemplary micro-drug pumps suitable for use as described herein include, but are not necessarily limited to, those disclosed in U.S. Pat. Nos. 5,234,692; 5,234,693; 5,728,396; 6,368,315; 6,666,845; and 6,620,151. All of these listed patents are incorporated herein by reference in their respective entireties.

In some embodiments, the one or more drugs are infused chronically into the stimulation site. Additionally or alternatively, the one or more drugs may be infused acutely into the stimulation site in response to a biological signal or a sensed need for the one or more drugs.

The stimulator (140) of FIG. 1 is illustrative of many types of stimulators that may be used to apply a stimulus to a stimulation site. For example, the stimulator (140) may include an implantable pulse generator (IPG) coupled to one or more leads having a number of electrodes, a spinal cord stimulator (SCS), a cochlear implant, a deep brain stimulator, a drug pump (mentioned previously), a micro-drug pump (mentioned previously), or any other type of implantable stimulator configured to deliver a stimulus at a stimulation site within a patient. Exemplary IPGs suitable for use as described herein include, but are not limited to, those disclosed in U.S. Pat. Nos. 6,381,496; 6,553,263 and 6,760,626. Exemplary spinal cord stimulators suitable for use as described herein include, but are not limited to, those disclosed in U.S. Pat. Nos. 5,501,703; 6,487,446; and 6,516,227.

Exemplary cochlear implants suitable for use as described herein include, but are not limited to, those disclosed in U.S. Pat. Nos. 6,219,580; 6,272,382; and 6,308,101. Exemplary deep brain stimulators suitable for use as described herein include, but are not limited to, those disclosed in U.S. Pat. Nos. 5,938,688; 6,016,449 and 6,539,263. All of these listed patents are incorporated herein by reference in their respective entireties.

Alternatively, the stimulator (140) may include an implantable microstimulator, such as a BION® microstimulator (Advanced Bionics® Corporation, Valencia, Calif.). Various details associated with the manufacture, operation, and use of implantable microstimulators are disclosed in U.S. Pat. Nos. 5,193,539; 5,193,540; 5,312,439; 6,185,452; 6,164,284; 6,208,894 and 6,051,017. All of these listed patents are incorporated herein by reference in their respective entireties.

Figure 2:
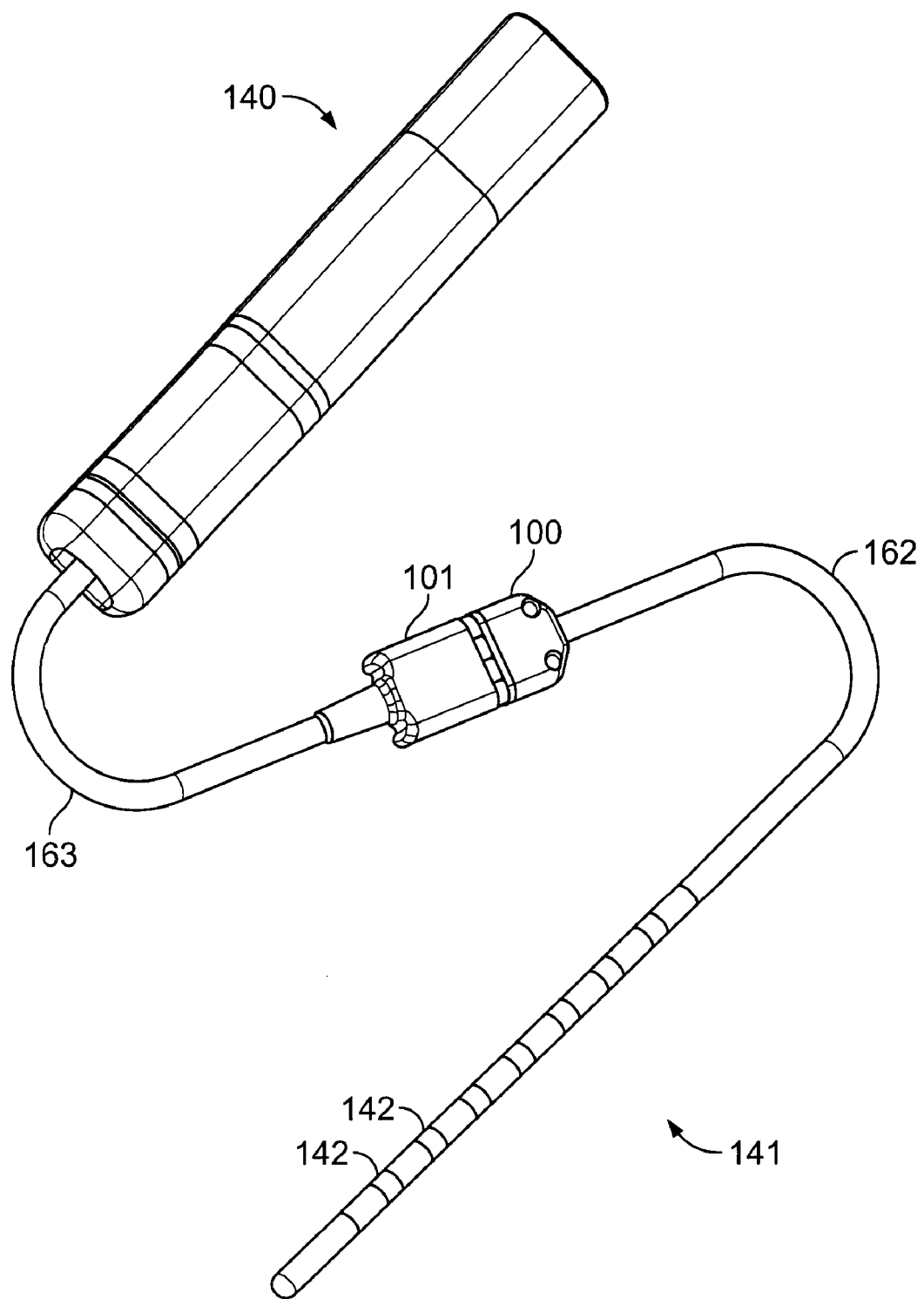
FIG. 2 illustrates an exemplary stimulator configured to electrically couple with a number of electrodes disposed on a lead according to principles described herein.

FIG. 2 illustrates an exemplary stimulator (140) configured to electrically couple with a number of electrodes (142) disposed on a lead (141). As shown in FIG. 2, a first connector assembly (100) and a second connector assembly (101) may facilitate the electrical connection between the electrodes (142) and the stimulator (140). In some examples, the first connector assembly (100) is coupled to the lead (141) via a first lead extension (162) and the second connector assembly (101) is coupled to the stimulator (140) via a second lead extension (163). It will be recognized that the lead extensions (162, 163) are optional and that the connector assemblies (100, 101) may be coupled directly to the lead (141) and/or stimulator (140). It will also be recognized that the stimulator (140) shown in FIG. 2 is merely illustrative of the many different types of implantable devices that may employ the use of the connector assemblies (100,101) described herein.

The connector assemblies (100, 101) may be used to electrically couple the stimulator (140) with many different types of devices. For example, the connector assemblies (100, 101) may be used to couple the stimulator (140) to a lead (142), as shown in FIG. 2. However, it will be recognized that the connector assemblies (100, 101) may additionally or alternatively be used to couple the stimulator (140) to any other type of device including, but not limited to, a sensor, another implantable device, and/or an external device.

In some examples, one of the connector assemblies (100, 101) includes a male connector assembly and one of the connector assemblies (100, 101) includes a female or receptacle connector assembly. Exemplary male connector assemblies and receptacle connector assemblies will be described in more detail below.

Figure 3:
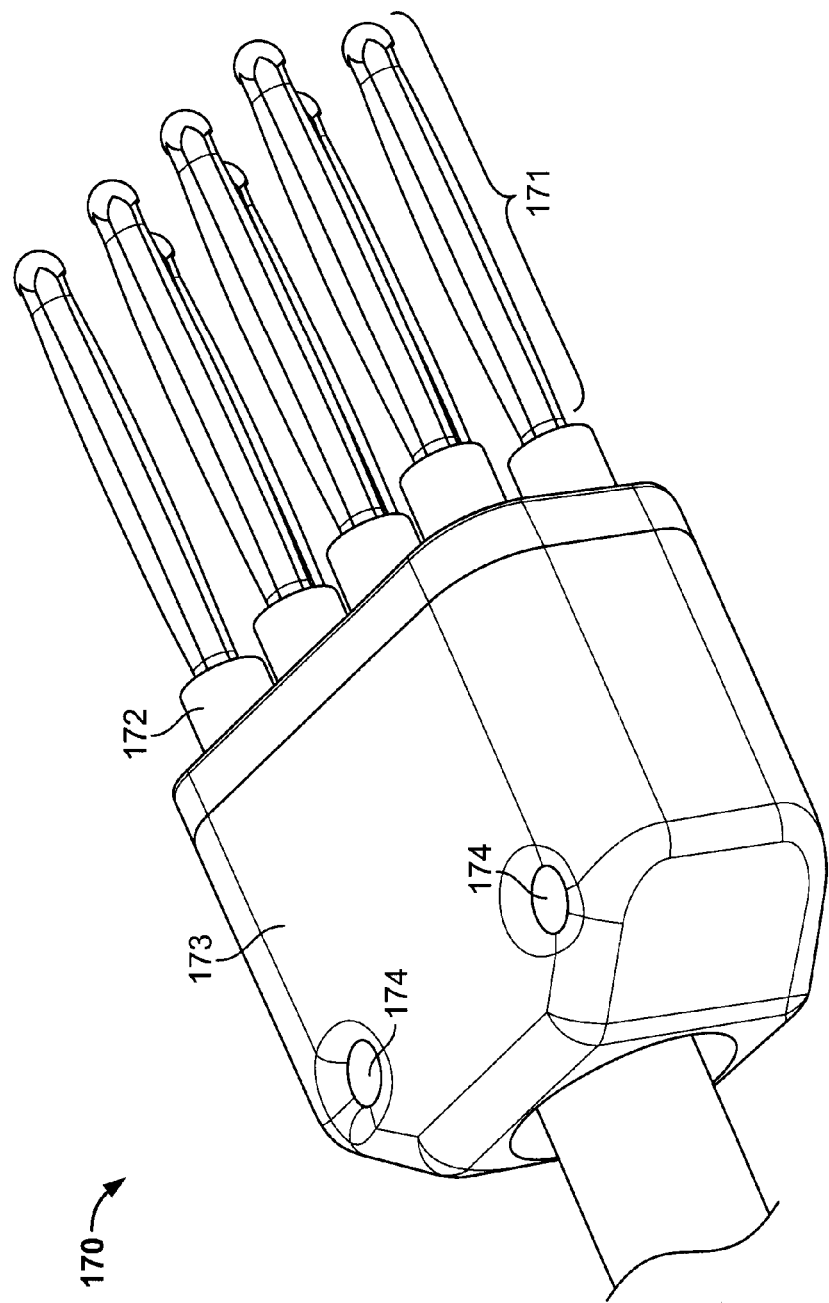
FIG. 3 is a perspective wireframe view of an exemplary male connector assembly according to principles described herein.

FIG. 3 is a perspective wireframe view of an exemplary male connector assembly (170). As shown in FIG. 3, the male connector assembly (170) includes an array of plug contacts (171), a number of overmolds (172) configured to house a proximal portion of each of the plug contacts (171), and a housing (173) configured to house each of the overmolds (172) and one or more conductive paths (e.g., wires) that facilitate electrical connection between the plug contacts (171) and electrical circuitry within an implantable device, lead, lead extension, cable, or any other device. The housing (173) may be made out of any suitable material such as, but not limited to, plastic, ceramic, metal, etc. Moreover, the male connector assembly (170) may include any number of plug contacts (171) as best serves a particular application. The plug contacts (171) and overmolds (172) will be described in more detail below.

Figure 4:
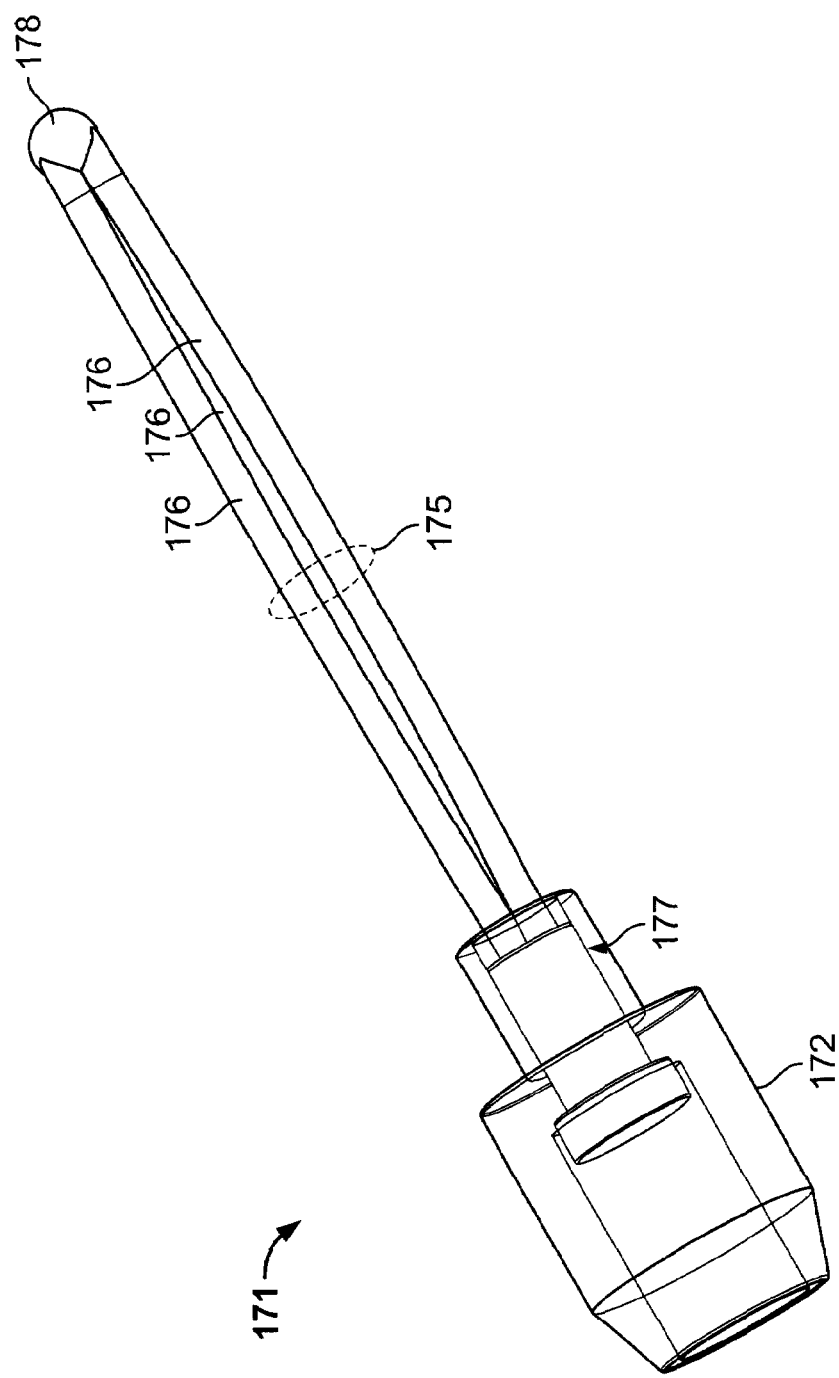
FIG. 4 is a perspective view of an exemplary plug contact according to principles described herein.

FIG. 4 is a perspective view of an exemplary plug contact (171). In some examples, as shown in FIG. 4, the plug contact (171) includes a multi-wire assembly (175) configured to mate with a corresponding socket within a receptacle connector assembly. The multi-wire assembly (175) may include two or more wires (176) as best serves a particular application. For example, the multi-wire assembly (175) may include three wires (176), as shown in FIG. 4.

Each wire (176) within the multi-wire assembly (175) may be made out of any suitable conductive material as best serves a particular application. For example, the wires (176) may be made out of a noble or refractory metal or compound such as, but not limited to, platinum, iridium, tantalum, titanium, titanium nitride, stainless steel, nickel, niobium or alloys of any of these. In some examples, one or more of the wires (176) may be hard-drawn. Moreover, each of the wires (176) may have any diameter as best serves a particular application.

As shown in FIG. 4, each wire (176) within the multi-wire assembly (175) may be joined at is respective proximal end to a holding sleeve (177). In some examples, the holding sleeve (177) is conductive and the wires (176) are conductively joined thereto. The wires (176) may be joined at their respective proximal ends to the holding sleeve (177) using any suitable method including, but not limited to, laser welding, brazing, soldering, bonding with conductive epoxy, or crimping. The holding sleeve (177), in turn, may be electrically coupled to one or more conductive paths within the male connector assembly (170).

In some alternative examples, the wires (176) may be conductively joined together at their proximal ends without the use of the holding sleeve (177). For example, the wires (176) may be crimped together and electrically coupled to one or more conductive paths within the male connector assembly (170). However, for illustrative purposes only, it will be assumed in the examples given herein that a conductive holding sleeve (177) is used to join the wires (176) together at their respective proximal ends.

In some examples, the holding sleeve (177) and wires (176) are made out of the same material. However, it will be recognized that the holding sleeve (177) may be made out of any conductive material as best serves a particular application.

As shown in FIG. 4, the distal tips of each of the wires (176) within the multi-wire assembly (175) are conductively joined together. For example, as shown in FIG. 4, the distal tips of each of the wires (176) may be welded, soldered, brazed, or otherwise conductively bonded to a conductive joint (178).

In some examples, the wires (176) are at least partially flexible such that when the wires (176) are joined to the holding sleeve (177) and at their distal tips, the wires (176) concave outwardly, as shown in FIG. 4. As will be described in more detail below, the wires (176) are also compressible so as to allow insertion of the multi-wire assembly (175) into a corresponding socket.

In some examples, the holding sleeve (177) may be hermetically surrounded by an overmold (172). The overmold (172) may be made out of a relatively hard material such as, but not limited to, plastic, thermoplastic, ceramic, or any other suitable material. For example, exemplary thermoplastics that may be used include, but are not limited to, PEEK and Hysol, which are inert to all common solvents and resist a wide range of organic and inorganic liquids. The overmold (172) may be hermetically coupled to the holding sleeve (177) using any suitable process such as, but not limited to, brazing, co-firing, laser welding, molding, and/or bonding with an epoxy.

Figure 5:
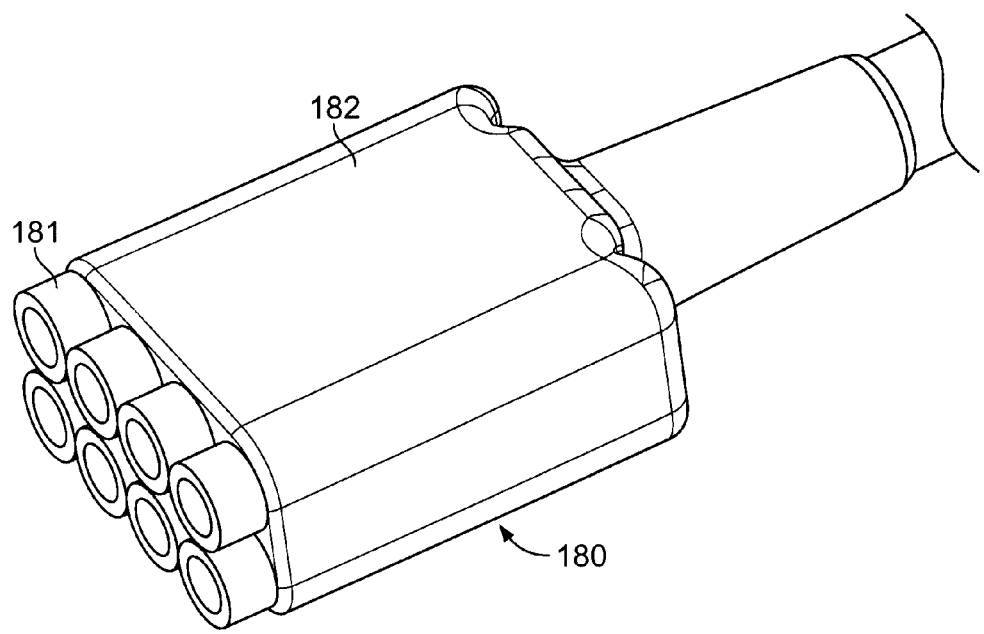
FIG. 5 is a perspective wireframe view of an exemplary receptacle connector assembly configured to mate with the male connector assembly of FIG. 3 according to principles described herein.

FIG. 5 is a perspective wireframe view of an exemplary receptacle connector assembly (180) configured to mate with the male connector assembly (170) of FIG. 3. As shown in FIG. 5, the receptacle connector assembly (180) includes a number of socket assemblies (181) each configured to mate with a corresponding plug contact (171). The receptacle connector assembly (180) may also include a housing (182) configured to house each of the socket assemblies (181). The housing (182) may be made out of any suitable material such as, but not limited to, plastic, ceramic, metal, etc. The socket assemblies (181) will be described in more detail below.

Figure 6:
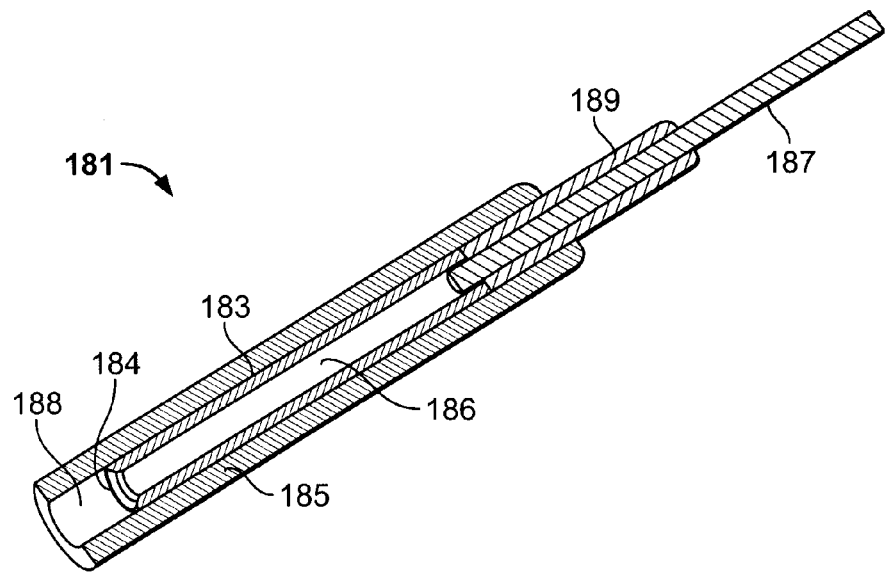
FIG. 6 is a perspective view of an exemplary socket assembly according to principles described herein.

FIG. 6 is a perspective view of an exemplary socket assembly (181). As shown in FIG. 6, a socket (183) having a tapered opening (184) at a distal end may be surrounded by an overmold (185). The socket (183) may be made out of any conductive material(s) as best serves a particular application. For example, the socket (183) may be made out of a noble or refractory metal or compound such as, but not limited to, platinum, iridium, tantalum, titanium, titanium nitride, stainless steel, nickel, niobium or alloys of any of these. In some examples, the socket (183) is made out of the same material as the multi-wire assembly (175).

As shown in FIG. 6, the socket (183) includes a hollow lumen (186) extending at least partially therethrough into which a corresponding multi-wire assembly (175) of a plug contact (171) may be inserted. As will be described in more detail below, the perimeter of the inner wall or surface of the socket (183) may be slightly smaller than the perimeter of the multi-wire assembly (175) in an uncompressed state so as to maintain electrical contact therebetween when the multi-wire assembly (175) is inserted within the socket (183).

As shown in FIG. 6, a conductive wire (187) may be electrically joined to a proximal portion of the socket (183). The conductive wire (187) may be conductively joined to the socket (183) using any suitable method including, but not limited to, laser welding, brazing, soldering, or bonding with conductive epoxy. The conductive wire (187) may then be used to electrically couple the socket (183) with an electrode, electronic circuitry within an implantable device, or any other component.

As mentioned, the socket (183) is surrounded by an overmold (185). In some examples, the overmold (185) is made out of a material that has shape memory such as, but not limited to, silicone. In this manner, as will be described in more detail below, a hermetic seal may be formed when a corresponding plug contact (171) is inserted into the socket (183). The overmold (185) may be hermetically coupled to the socket (183) using any suitable process such as, but not limited to, brazing, co-firing, laser welding, molding, and/or bonding with conductive epoxy.

As shown in FIG. 6, the overmold (185) may include an extended tubular section (188) that extends distally beyond the distal end of the socket (183). As will be described in more detail below, the extended tubular section (188) serves to ensure a hermetic seal between the socket (183) and a corresponding plug contact (171). The overmold (185) may also include an extended tubular section (189) that extends proximally beyond the proximal end of the socket (183). The extended tubular section (189) provides strain relief for the conductive connection between the conductive wire (187) and the socket (183).

Figure 7:
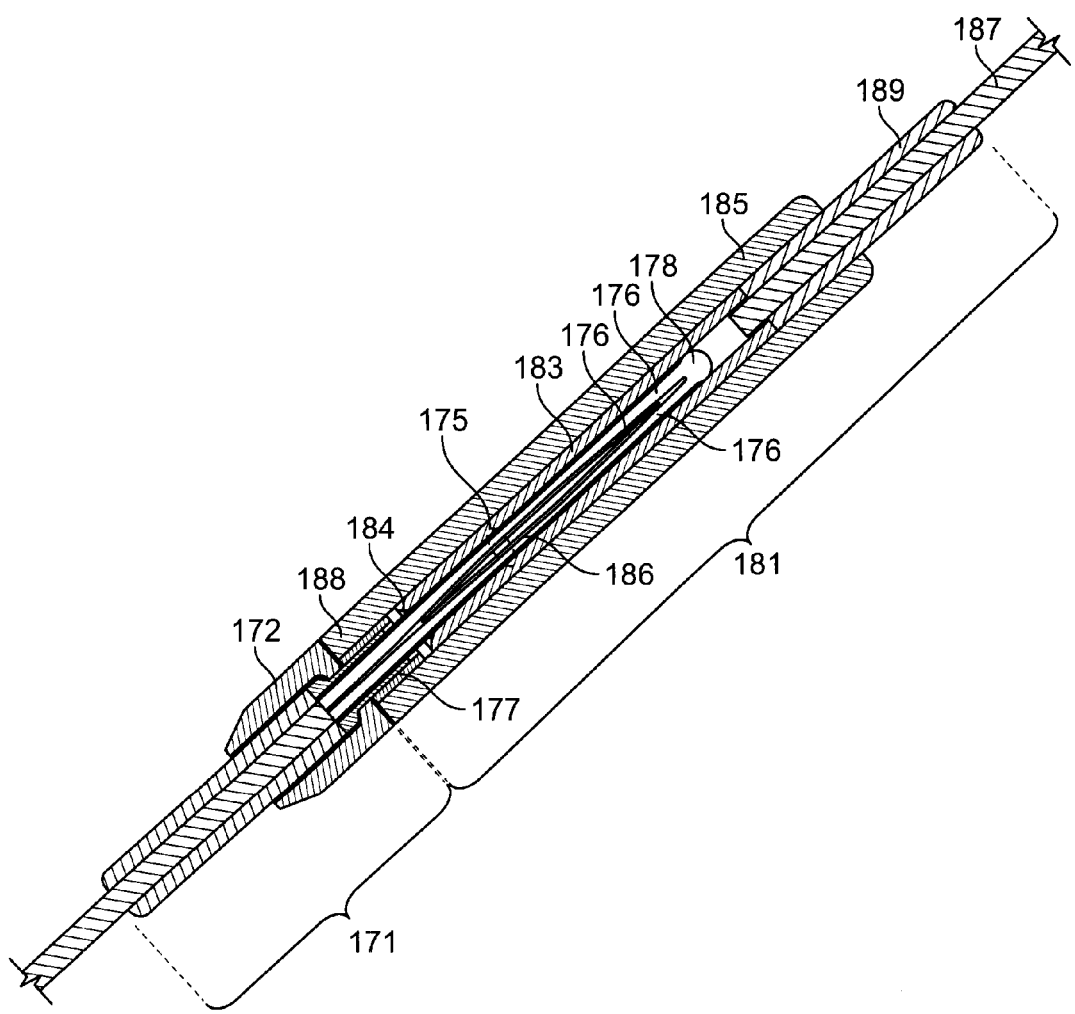
FIG. 7 is a cross-sectional view of a plug contact inserted within a socket assembly according to principles described herein.

FIG. 7 is a cross-sectional view of a plug contact (171) inserted within a socket assembly (181). As shown in FIG. 7, the multi-wire assembly (175) has been inserted within the lumen (186) of the socket (183). As mentioned, the perimeter of the inner wall of the socket (183) may be slightly smaller than the perimeter of the multi-wire assembly (175) in an uncompressed state. Hence, the tapered opening (184) of the socket (183) is configured to compress the multi-wire assembly (175) as the multi-wire assembly (175) is inserted into the lumen (186) of the socket (183). The compressed state of the multi-wire assembly (175) within the lumen (186) of the socket (183) maintains electrical contact between the inner wall of the socket (183) and the multi-wire assembly (175).

In some alternative examples, the length of the multi-wire assembly (175) is such that the base of the lumen (186) exerts pressure against the conductive joint (178) when the multi-wire assembly (175) is inserted within the lumen (186) of the socket (183). The exerted pressure causes the wires (176) to bend outwardly until they come in contact with the inner wall of the socket (183). In this manner, electrical contact between the inner wall of the socket (183) and the multi-wire assembly (175) may alternatively be maintained.

In some examples, the plug contact (171) and socket assembly (181) are constructed so as to create a hermetic seal when mated to prevent water vapor, gas, bacteria, and/or other biological substances from coming in contact with the multi-wire assembly (175) and/or socket (183). For example, the extended tubular section (188) of the socket overmold (185) may be configured to tightly engage the holding sleeve (177) of the plug contact (171) when the plug contact (171) is inserted within the socket assembly (181). Moreover, the material of the socket overmold (185) (e.g., silicone) interacts with the relatively harder material of the plug overmold (172) so as to further create a hermetic seal between the plug contact (171) and the socket assembly (181).

Figure 8:
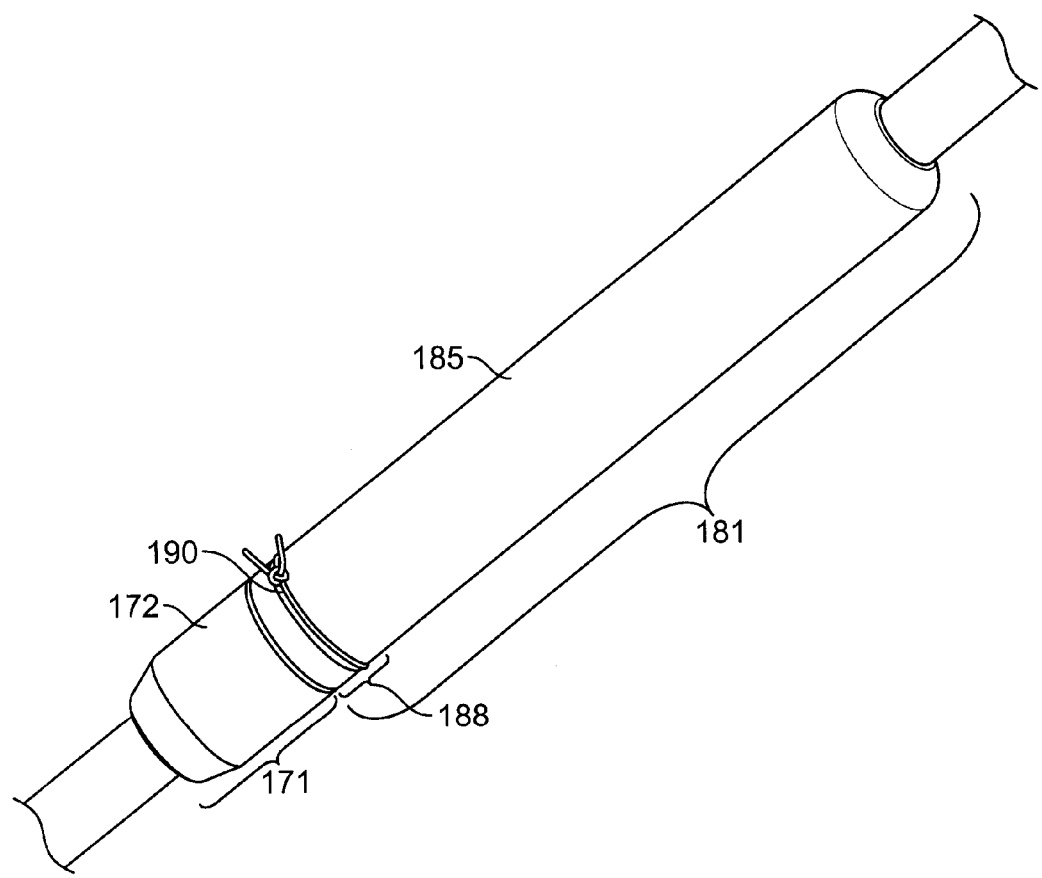
FIG. 8 is a perspective view of the plug contact inserted within the socket assembly according to principles described herein.

In some examples, the plug contact (171) may be further secured within the socket assembly (181) with one or more sutures, clamps, or other securing devices that are placed around the outer surface of the socket overmold (185) and/or plug overmold (172). For example, FIG. 8 is a perspective view of the plug contact (171) inserted within the socket assembly (181). As shown in FIG. 8, a suture (190) may be tied around the extended tubular section (188) of the socket overmold (185) in order to secure the plug contact (171) within the socket assembly (181). Because the socket overmold (185) has shape memory, the pressure exerted by the suture (190) presses the extended tubular section (188) of the socket overmold (185) against the holding sleeve (177), which is located within the socket overmold (185), and thereby secures the plug contact (171) within the socket assembly (181). It will be recognized that the suture (190) shown in FIG. 8 is merely illustrative of the many different types of securing devices that may be used to secure the plug contact (171) within the socket assembly (181). Moreover, it will be recognized that any number of securing devices may be used to secure the plug contact (171) within the socket assembly (181).

Figure 9:
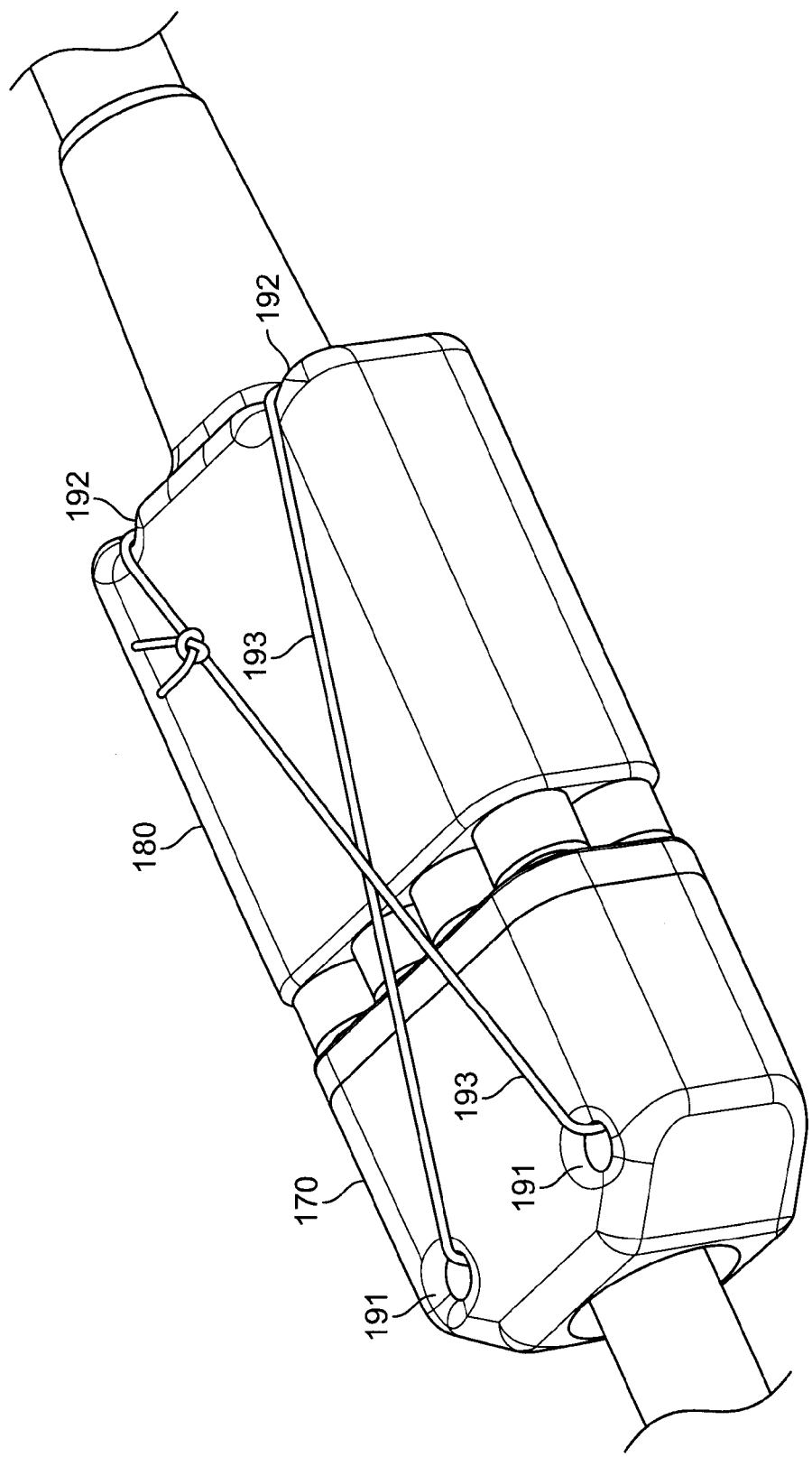
FIG. 9 is a perspective view of a securing device configured to secure the exemplary male connector assembly to the exemplary receptacle connector assembly according to principles described herein.

Once the exemplary male connector assembly (170) and the exemplary receptacle connector assembly (180) have been connected together, one or more securing devices may be used to prevent the connector assemblies (170, 180) from disconnecting. For example, FIG. 9 is a perspective view of the exemplary male connector assembly (170) connected to the exemplary receptacle connector assembly (180). As shown in FIG. 9, one of the connector assemblies (e.g., the male connector assembly (170)) may include one or more holes (191) extending at least partially therethrough. The holes (191) may have any suitable shape and/or size as best serves a particular application.

In some examples, as shown in FIG. 9, one or more surgical ties (193) may be threaded through the holes (191) and around both of the connector assemblies (170, 180) to prevent the connector assemblies (170, 180) from disconnecting. One or more guide tracks (192) may be built into the surface of one or more of the connector assemblies (170, 180) to facilitate proper placement of the surgical ties (193). It will be recognized that one or more anchors, hooks, sutures, or other affixing devices may be used to prevent the connector assemblies (170, 180) from disconnecting. Moreover, it will be recognized that while two holes (191) and two guide tracks (192) are shown in FIG. 9, any number of holes (191) and guide tracks (192) may be included in one or both of the connector assemblies (170, 180).

Figure 10B:
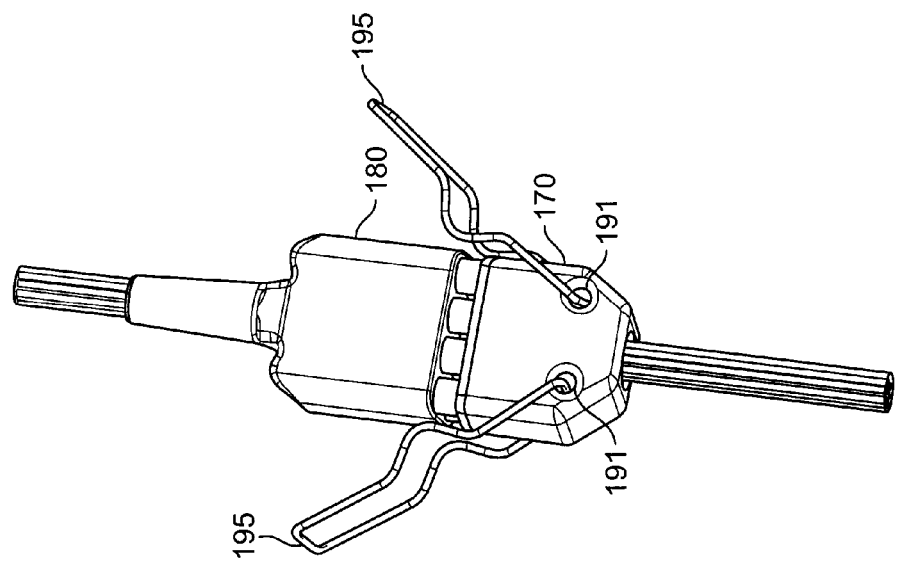
FIGS. 10A-10D illustrate another exemplary securing device that may be used to prevent the connector assemblies from disconnecting according to principles described herein.
Figure 10A:
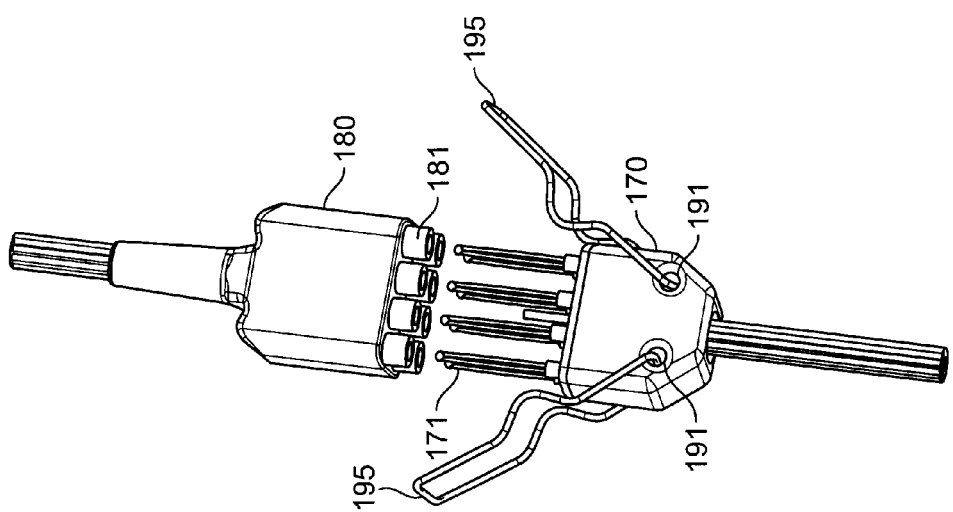

FIGS. 10A-10D illustrate another exemplary securing device that may be used to prevent the connector assemblies (170, 180) from disconnecting. As shown in FIG. 10A, one or more clips (195) may be inserted into one or more of the holes (191) within the body of one of the connector assemblies (e.g., the male connector assembly (170)). The clips (195) may have any suitable shape and size and may be made out of any suitable material as best serves a particular application. In some examples, the clips (195) are made out of a memory shape alloy (e.g., an alloy of titanium nitride).

Figure 10C:
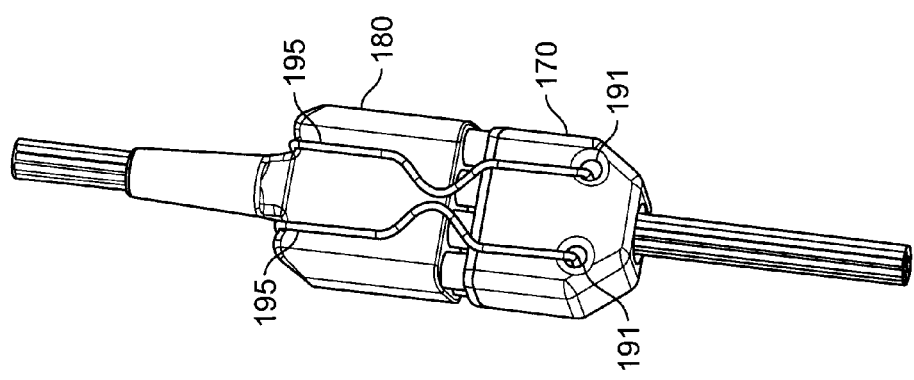
Figure 10D:
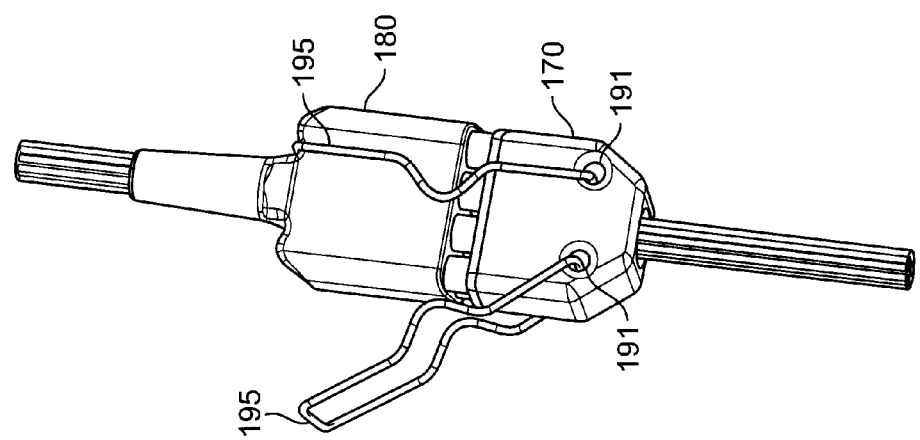

The plug contacts (171) may then be inserted into corresponding socket assemblies (181) of the receptacle connector assembly (180), as shown in FIG. 10B. The clips (195) may then be placed over the receptacle connector assembly (180), as shown in FIGS. 10C-10D. The clips (195) are advantageous in many applications wherein it is desirable to be able to quickly connect and/or disconnect the connector assemblies (180).

The preceding description has been presented only to illustrate and describe embodiments of the invention. It is not intended to be exhaustive or to limit the invention to any precise form disclosed. Many modifications and variations are possible in light of the above teaching.

What is claimed is:

1. A system comprising:
   a receptacle connector assembly comprising one or more socket assemblies each having a socket with an at least partially conductive inner surface;
   a male connector assembly comprising one or more plug contacts configured to mate with said sockets; and
   a hermetic seal between the receptacle connector assembly and the male connector assembly,
   wherein
      each of said plug contacts comprises a multiplicity of flexible wires fixedly joined together at a distal tip such that when said plug contacts are within said sockets, said flexible wires make electrical contact with said at least partially conductive inner surfaces of said sockets, and
      the hermetic seal is effective to hermetically seal the plug contacts and the sockets with said plug contacts disposed within said sockets.

2. The system of claim 1, wherein:
   each of said plug contacts further comprises a holding sleeve; and
   said multiplicity of flexible wires are encompassed within said holding sleeve and thereby joined at their proximal ends.

3. The system of claim 1, wherein:
   each of said socket assemblies further comprises a first overmold surrounding said socket; and
   said first overmold comprises a material that has shape memory.

4. The system of claim 3, wherein said material of said first overmold comprises silicone.

5. The system of claim 3, wherein:
   said first overmold comprises an extended tubular section extending distally beyond a distal end of said socket; and
   said extended tubular section is configured to make the hermetic seal between said socket and one of said plug contacts.

6. The system of claim 3, wherein:
   said first overmold comprises an extended tubular section extending proximally beyond a proximal end of said socket; and
   said extended tubular section is configured to provide strain relief for said socket.

7. The system of claim 3, wherein each of said plug contacts further comprises:
   a holding sleeve, wherein said multiplicity of flexible wires are joined at a proximal end to said holding sleeve; and
   a second overmold configured to at least partially house said holding sleeve;
   wherein said second overmold comprises at least one or more of a plastic material, a thermoplastic material, and a ceramic material.

8. The system of claim 7, wherein said first overmold and said second overmold are configured to interact to create the hermetic seal with said receptacle connector assembly and said male connector assembly mated.

9. The system of claim 1, wherein each of said sockets comprise a tapered opening configured to compress said flexible wires of said plug contacts when said plug contacts are inserted into said sockets.

10. The system of claim 1, further comprising one or more securing devices figured to prevent said receptacle connector assembly and said male connector assembly from disconnecting.

11. The system of claim 10, wherein said one or more securing devices comprises at least one or more of a clip, a suture, a surgical tie, a hook, and an anchor.

12. The system of claim 1, wherein each of the socket assemblies is dimensioned to receive the mating plug contact and, during the insertion of the plug contact into the socket assembly, apply a longitudinal force to the distal tip where the multiplicity of flexible wires are fixedly joined together such that the flexible wires are pressured laterally outward.

13. A male connector assembly configured to mate with a receptacle connector assembly having a collection of socket assemblies each having a socket with an at least partially conductive inner surface and an longitudinally directed inner sealing surface that extends beyond the at least partially conductive inner surface, said male connector assembly comprising:
   a collection of longitudinally extending elongate plug contacts, each positioned to mate with a corresponding socket,
   wherein each of said plug contacts comprises
      a multiplicity of elongate flexible wires joined together at a distal tip such that when said plug contacts are within said sockets, said flexible wires make electrical contact with said at least partially conductive inner surfaces of said sockets, and
      a longitudinally directed outer sealing surface disposed proximally of at least a portion of the flexible wires, wherein the outer sealing surface is dimensioned to hermetically seal with said inner sealing surface of said sockets.

14. The male connector assembly of claim 13, wherein:
   each of said plug contacts further comprises a conductive holding sleeve; and
   said multiplicity of flexible wires are encompassed within said conductive holding sleeve and thereby joined at their proximal ends.

15. The male connector assembly of claim 14, wherein:
   each of said plug contacts comprises an overmold configured to at least partially house said holding sleeve;

said overmold comprises said longitudinally directed outer sealing surface; and said longitudinally directed outer sealing surface comprises at least one or more of a plastic material, a thermoplastic material, and a ceramic material.

16. The male connector assembly of claim 15, wherein said overmold comprises at least one or more of PEEK and Hysol.

17. The male connector assembly of claim 13, further comprising one or more securing devices coupled to said male connector assembly and configured to prevent said male connector assembly and said receptacle connector assembly from disconnecting.

18. The male connector assembly of claim 13, wherein each of the sockets is dimensioned to receive the mating plug contact and, during the insertion of the plug contact into the socket, apply a longitudinal force to the distal tip where the multiplicity of elongate flexible wires are joined together such that the flexible wires are pressured laterally outward.

19. A system comprising:
a male connector assembly comprising an elongate plug having a proximal end and a distal end, wherein the plug comprises
a collection of flexible, elongate, longitudinally extending conductive members, and
a joint that fixedly joins the conductive members together,
wherein
the conductive members are curved so that, before insertion, the conductive members curve laterally outward from a first position to return laterally inward to a second position,
the first position, the second position, and the joint are longitudinally arranged along the plug, and
the first position is proximal to both the second position and the joint;
a female receptacle connector assembly that defines a socket with an at least partially conductive inner surface, wherein the socket is dimensioned to receive the plug and, during the insertion of the plug into the socket, apply a longitudinal force to the joint such that the conductive members, in accordance with their curvature, are pressured laterally outward to ensure contact with the inner surface of the socket.

20. The system of claim 19, wherein the socket comprises a base that is positioned and dimensioned to block passage of the joint during the insertion and thereby apply the longitudinal force to the plug to pressure the conductive members laterally outward.

21. The system of claim 19, wherein the joint is longitudinally displaceable during insertion in response to the longitudinal force applied during insertion.

22. The system of claim 19, wherein the joint is disposed at a distal end of the plug.

23. The system of claim 19, wherein the plug defines an elongate void in between the conductive members.

24. The system of claim 23, wherein the elongate void extends longitudinally at least between the first position and the second position.

25. The system of claim 19, further comprising a hermetic seal between the male connector assembly and the female receptacle connector assembly.

26. The system of claim 19, wherein the second position is positioned at the joint.

\* \* \* \* \*